United States Patent [19]

Roberts

[11] Plant 4,112

[45] Sept. 27, 1977

[54] AZALEA PLANT NAMED COTTON CANDY

[75] Inventor: Alfred N. Roberts, Corvallis, Oreg.

[73] Assignee: Geo. J. Ball, Inc., West Chicago, Ill.

[21] Appl. No.: 728,952

[22] Filed: Oct. 1, 1976

[51] Int. Cl.[2] ..... A01H 5/00

[52] U.S. Cl. ..... Plt./56

[58] Field of Search ..... Plt./55-56

*Primary Examiner*—Robert E. Bagwill

*Attorney, Agent, or Firm*—Rummler and Snow

[57] ABSTRACT

A new variety of hybrid azalea plant particularly suited for greenhouse forcing because of its vigorous and well branching growth habits, its prolific breaking, and its abundant production of ruffled and semi-double blossoms of delicate shell pink and creamy white coloration.

1 Drawing Figure

BACKGROUND OF THE INVENTION

This new variety of azalea plant was discovered by me in 1961 as a result of breeding efforts carried on by me at Oregon State University, Corvallis, Oreg., with the objective of producing an improved pot-forcing greenhouse azalea having better flowering and keeping qualities. This plant originated as a seedling of Albert and Elizabeth (unpatented) × Satin Robe (unpatented) and was selected by me for propagation and test because of its vigorous and well branched, but compact, growth habit and the very unusual delicate shell pink and creamy white coloring of its flowers.

Asexual propagation of this new plant was carried on by me and under my direction by means of cuttings at Corvallis, Oreg., and many successive generations of this plant have demonstrated that its distinctive and commercially advantageous characteristics are firmly fixed and hold true from generation to generation.

DESCRIPTION OF THE DRAWINGS

My new variety of azalea is illustrated by the accompanying photographic drawing in which the upper view shows a typical specimen of the potted plant in full bloom and the lower view shows details of a typical bud and the fully opened flower. The drawing views are prints which show the flower colors as nearly true as can be obtained by conventional photographic procedures and the true colors are shown by the hand painted swatches mounted below the lower view, the left hand swatch showing the Camelia Rose color of the petal margins and reverse sides and the right hand swatch showing the Neyron Rose color of the lower body portion of the petals.

DESCRIPTION OF THE NEW PLANT

The following is a detailed description of my new azalea plant with the color designations given according to the Horticultural Colour Chart produced by Robert S. Wilson and published by The Royal Horticultural Society of London, England.

THE PLANT

Origin: Seedling.

Parentage:

*Seed parent.*—Albert and Elizabeth (unpatented).

*Pollen parent.*—Satin Robe (unpatented).

Classification:

*Botanic.*—Rhododendron.

*Commercial.*—Hybrid Azalea.

Form: Bush — compact potted plant.

Growth: Vigorous, upright and profusely branching.

Strength: Sturdy and limber.

Foliage: Quantity — moderate.

*Size of leaf.*—¾ to 2 inches long × 3/16 to 1 inch wide.

*Shape.*—Elliptic with acute tip.

*Texture.*—Leathery.

*Aspect.*—Pubescent and glossy.

*Color.*—Mature leaves: Upper side — Ivy Green 0001060/3 through Spinach Green 0960. Under side — Spinach Green 0960/2. Young leaves: Upper side — Scheeles Green 860/2. Under side — Scheeles Green 860/3 with silvery white down.

*Ribs and veins.*—Netted, center rib on under side of leaf and very tomentose.

*Rachis.*—Flat topped and hirsute. On new leaves the hair is silvery. On mature leaves the hair is brown.

THE BUD

Form: Elliptical and pointed.

Size: Medium. 1⅛ to 1½ inches long. ½ to ¾ inch in diameter.

Opening: Bud opens slowly.

Color: When sepals first divide — Shades of Jasper Red 018/2 through 018 on each petal. When sepals being to unfurl — Camelia Rose 622/1.

Sepals: Upstanding.

*Color.*—Inside — Lettuce Green 861/3 through 861. Outside — Lettuce Green 861/2 through 861.

Calyx: Shape — Funnel-shaped; splits to star-shaped.

*Size.*—Small.

*Aspect.*—Hairy.

Peduncle: Length — ¼ to ⅜ inch. Erect and hairy.

*Color.*—Lettuce Green 861/3 near sepals shading to Majolica Yellow 09/2 at base.

THE FLOWER

Blooming habit: Profusely and normally in the Spring. This plant can be forced to bloom at any time. time.

Size of flower: Medium.

Borne: In clusters.

Shape: Funnel-form when bloom first opens. Shape becomes flatter and more open as flower matures.

Petalage: Number of petals — 5 main petals with up to 7 petaloids.

*Arrangement.*—Connate.

*Form.*—Semi-double with ruffled and puckered petals.

*Color.*—Outer petal — Camellia Rose 622/2 at margins and Neyron Rose 623/3 faintly streaked with Naples Yellow 403/3 in lower body portion. Inside petals — Camellia Rose 622/2. Reverse side — Camellia Rose 622/2 to 622/1.

*Texture.*—Soft.

*Appearance.*—Satiny.

*Petaloids.*—Number varies from 0 to 7 and petaloids are of various sizes. They may be connate and sometimes they are adnate and fused to the stamens.

*Color.*—Camellia Rose 622/2 to Neyron Rose 623/3 at the base.

Peduncle: Length ¼ to ½ inch. Sturdy and upright.

*Color.*—Uranium Green 63/3.

Fragrance: None.

Discoloration (after full bloom): The flower fades slightly and then darkens as petals dry.

Persistence: The flowers hang on and dry.

Lasting Quality: Very good.

REPRODUCTIVE ORGANS

Stamens:

*Anthers.*—5 in number, 1/16 inch long and in dorsifixed arrangement.

*Filaments.*—1 to 1¼ inches long. Color: Camellia Rose 622/1.

Pistils: One only.

*Style.*—1¾ inches long.

*Stigma.*—Color — Mimosa Yellow 602/2.

Ovaries: Superior and wooly.

My new variety of azalea plant is particularly distinguished by its very floriferous habit and the shell pink and cream white coloring of its flowers. The semi-double blossoms are also unique in their puckered satiny texture and the abundance of their production. This new variety is distinctive in its vigorous, well branching growth habit, its very prolific breaking which makes it ideally suited for greenhouse forcing, and in the excellent lasting quality of the blooming plant.

I claim:

1. A new and distinctive variety of azalea plant substantially as herein shown and described, characterized by its prolific production of delicate pink and creamy white, ruffled and puckered, semi-double blossoms; and by its vigorous, well branched growth habit under pot-forcing procedures in greenhouse culture.

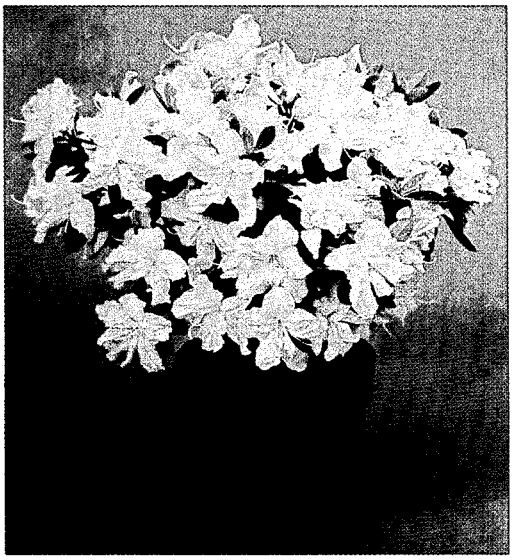
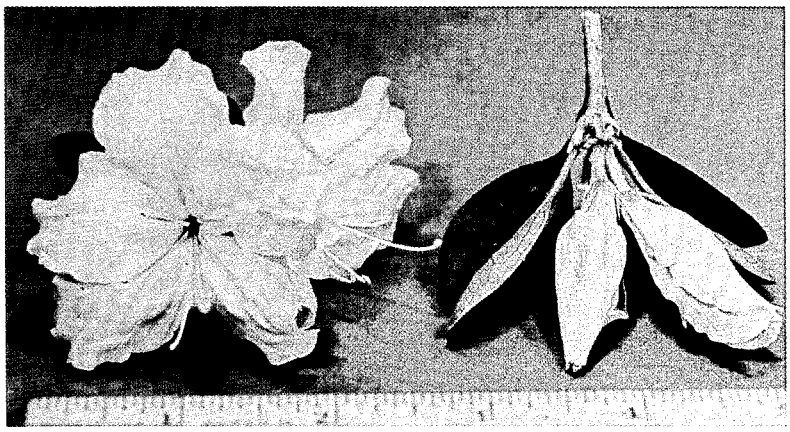

* * * * *